(12) United States Patent
Matsuda et al.

(10) Patent No.: US 7,709,818 B2
(45) Date of Patent: May 4, 2010

(54) PARTICLE BEAM IRRADIATION APPARATUS AND PARTICLE BEAM IRRADIATION METHOD

(75) Inventors: Koji Matsuda, Hitachi (JP); Kazuo Hiramoto, Hitachiohta (JP); Kunio Moriyama, Hitachi (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 11/239,073

(22) Filed: Sep. 30, 2005

(65) Prior Publication Data

US 2006/0076515 A1    Apr. 13, 2006

(30) Foreign Application Priority Data

Sep. 30, 2004 (JP) .............................. 2004-286234
Mar. 30, 2005 (JP) ................................ 2005-96672

(51) Int. Cl.
    A61N 5/10    (2006.01)
(52) U.S. Cl. .............. 250/492.3; 250/505.1; 250/423 R; 250/398; 315/503
(58) Field of Classification Search ................ 57/749.1; 250/492.3, 505.1, 423 R, 398; 315/503
See application file for complete search history.

(56) References Cited

U.S. PATENT DOCUMENTS

| | | | | |
|---|---|---|---|---|
| 4,870,287 A * | 9/1989 | Cole et al. | ............... | 250/492.3 |
| 5,260,581 A * | 11/1993 | Lesyna et al. | ............ | 250/492.3 |
| 5,585,642 A * | 12/1996 | Britton et al. | ............ | 250/492.3 |
| 5,818,058 A * | 10/1998 | Nakanishi et al. | ........ | 250/492.3 |
| 5,969,367 A | 10/1999 | Hiramoto et al. | | |
| 6,265,837 B1 * | 7/2001 | Akiyama et al. | ............ | 315/503 |
| 6,316,776 B1 * | 11/2001 | Hiramoto et al. | .......... | 250/492.3 |
| 6,777,700 B2 | 8/2004 | Yanagisawa et al. | | |
| 6,800,866 B2 * | 10/2004 | Amemiya et al. | ........ | 250/505.1 |
| 6,894,300 B2 * | 5/2005 | Reimoser et al. | ......... | 250/505.1 |
| 2002/0033456 A1 * | 3/2002 | Tachikawa et al. | .......... | 250/398 |
| 2002/0128807 A1 * | 9/2002 | Sakamoto et al. | .............. | 703/5 |
| 2004/0118081 A1 * | 6/2004 | Reimoser et al. | ........... | 52/749.1 |

(Continued)

FOREIGN PATENT DOCUMENTS

EP    0 986 070 A1    3/2000

(Continued)

OTHER PUBLICATIONS

Pedroni, et al ("Latest Developments in Proton Therapy" Proceedings of EPAC 2000, Vienna, Austria, pp. 240-244).*

(Continued)

*Primary Examiner*—David A Vanore
*Assistant Examiner*—Michael Maskell
(74) *Attorney, Agent, or Firm*—Dickstein Shapiro LLP

(57) ABSTRACT

To ensure irradiation accuracy and safety, even when an irradiation device employing a different irradiation method is used, disclosed is herein a charged particle beam irradiation apparatus that irradiates an irradiation target with charged particle beams includes:

a charged particle beam generator for generating the charged particle beams; a passive scattering irradiation device and a scanning irradiation device, both for irradiating the irradiation target with the charged particle beams; a beam transport system for transporting the charged particles beam extracted from the charged particle beam generator, to selected one of the two irradiation devices; and a central controller that modifies operating parameters on the charged particle beam generator, according to the irradiation method adopted for the selected irradiation device.

15 Claims, 5 Drawing Sheets

U.S. PATENT DOCUMENTS

2004/0164254 A1* 8/2004 Beloussov et al. ....... 250/492.1

FOREIGN PATENT DOCUMENTS

| JP | 09-223600 | 8/1997 |
|---|---|---|
| JP | 2833602 | 10/1998 |
| JP | 11-501232 | 2/1999 |
| JP | 2001-210498 | 8/2001 |
| WO | WO96/25201 | 8/1996 |

OTHER PUBLICATIONS

Jones, et al ("Magnetically scanned proton therapy beams: rationales and principles" Radiation Physics and Chemistry 61 (2001) 615-618).*

European Patent Notice of Opposition, Feb. 10, 2009.

Search Report and Written Opinion for EP 08001122.4.

CERN report, "Proton-Ion Medical Machine Study", Part I and Part II, (2000).

Y. Jongen, et al., "The Proton Therapy System for the NPTC: Equipment Description and Progress Report", *Nuclear Instruments and Methods in Physics Research*, B, vol. 113, pp. 522-525, (1996).

U. Amaldi, "Accelerators for Medical Applications," *5th European Accelerator Conference*, Jun. 10-14, 1996.

H. Reist, et al. "Concept for Handling and Service of the Proscan Degrader Unit," *Scientific and Technical Report*, vol. VI, pp. 109-112 (2003).

J.M. Schippers, et al. "Superconducting Cyclotron and Beam Lines of PSI's NEw Proton Therapy Facility," *Proscan*, (2004).

H. Resist, et al. "Fast Degrader to Set the Energies for the Application of the Depth Dose in Proton Therapy," *PSI Report*, (2001).

K. Noda, et al., "Slow Beam Extraction by a Traverse RF Field with AM and FM," Nuclear Instruments and Methods in Physics Research, A, vol. 374, pp. 269-277, (1996).

* cited by examiner

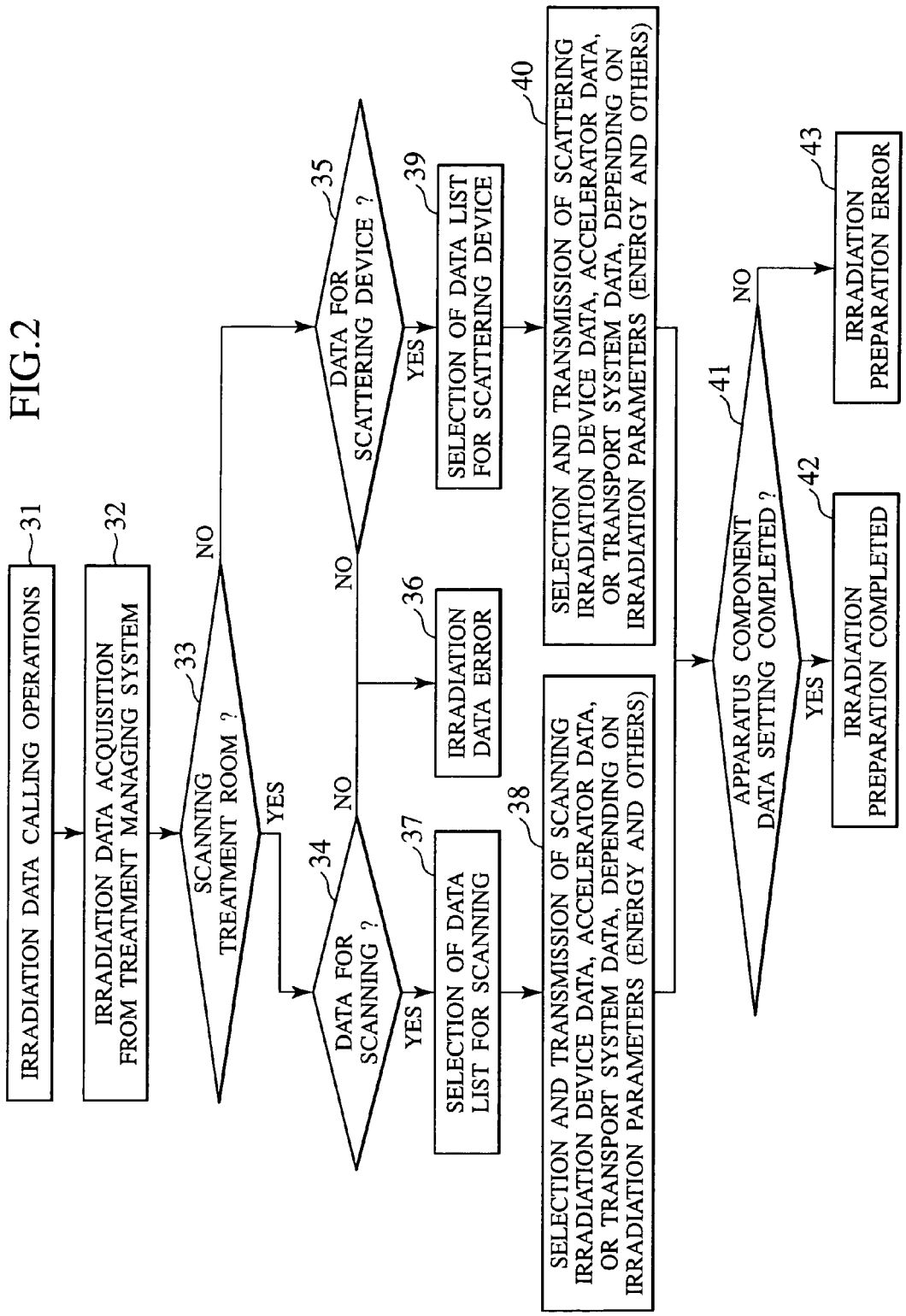

FIG.3

ACCELERATOR OPERATING PARAMETER DATA LIST FOR SCATTERING DEVICE

| ENERGY | MAGNET PATTERN ID | HIGH-FREQUENCY EXTRACTION POWER | BEAM INTENSITY UPPER LIMIT | SCRAPER POSITION | FREQUENCY RANGE | ... |
|---|---|---|---|---|---|---|
| 90 | P090 | 61 | 150 | 50 | ±25kHz | ... |
| 120 | P120 | 71 | 150 | 50 | ±25kHz | ... |
| 150 | P150 | 79 | 150 | 50 | ±25kHz | ... |
| 180 | P180 | 87 | 150 | 50 | ±25kHz | ... |
| 210 | P210 | 94 | 150 | 50 | ±25kHz | ... |
| 240 | P240 | 100 | 150 | 50 | ±25kHz | ... |

ACCELERATOR OPERATING PARAMETER DATA LIST FOR SCANNING

| ENERGY | MAGNET PATTERN ID | HIGH-FREQUENCY EXTRACTION POWER | BEAM INTENSITY UPPER LIMIT | SCRAPER POSITION | FREQUENCY RANGE | ... |
|---|---|---|---|---|---|---|
| 70 | P070 | 6 | 20 | 20 | ±5kHz | ... |
| 75 | P075 | 6 | 21 | 20 | ±5kHz | ... |
| .. | .. | .. | .. | .. | .. | ... |
| 226 | P226 | 23 | 71 | 20 | ±5kHz | ... |
| 228 | P228 | 24 | 72 | 20 | ±5kHz | ... |
| 230 | P230 | 25 | 73 | 20 | ±5kHz | ... |

|  | SCATTERING IRRADIATION METHOD | SCANNING IRRADIATION METHOD |
|---|---|---|
| BEAM INTENSITY SETTING VALUE | LARGE | SMALL |
| BEAM SIZE SETTING VALUE | MEDIUM | SMALL |
| ALLOWABLE ENERGY RANGE | LARGE | SMALL |
| ALLOWABLE BEAM POSITION RANGE | LARGE | SMALL |

PARTICLE BEAM IRRADIATION APPARATUS AND PARTICLE BEAM IRRADIATION METHOD

BACKGROUND OF THE INVENTION

The present invention relates to the particle beam irradiation apparatus and particle beam irradiation method used for irradiating affected regions with charged particle beams such as proton or carbon ion beams in order to provide medical care.

Among known medical treatment methods is one in which the affected regions of patients who are suffering from diseases such as cancer are irradiated with proton, carbon ion, or other charged particle beams. The large-scale charged particle beam irradiation apparatus used in this treatment method has a charged particle beam generator, a beam transport system, and a plurality of irradiation devices. A charged particle beam that has been accelerated by the charged particle beam generator reaches selected one of the plural irradiation devices through the beam transport system, and then the beam is emitted from the nozzle of the irradiation device to the affected region of the patient lying on a treatment couch. In general, for such a charged particle beam irradiation apparatus with a plurality of irradiation devices, these irradiation devices are connected to one charged particle beam generator and beams can be transported to a desired irradiation device by changing beam transport system data settings (refer to JP-A-11-501232, for example).

Passive scattering and pencil beam scanning are known irradiation methods. Passive scattering is an irradiation method in which beams are spread by a scattering device and then shaped to fit to the particular shape of the affected region, and pencil beam scattering is an irradiation method in which the inside of the affected region is scanned with narrow beams (refer to Japanese Patent No. 2833602, for example).

SUMMARY OF THE INVENTION

In general, the scanning method has the feature that an absorbed dose distribution more matching the shape of the affected region can be obtained than with the passive scattering method. Accordingly, practical use of the scanning method in medical care is increasing in recent years. Conventional charged particle beam irradiation apparatus with a plurality of irradiation devices has usually employed irradiation devices based on passive scattering. However, since practical use of the scanning method is increasing in recent years as mentioned above, charged particle beam irradiation apparatus with the plurality of irradiation devices which include irradiation devices of different irradiation schemes such as scanning and passive scattering is likely to be placed in practical use in the future.

The present inventors studied the scanning method and the passive scattering method to find out the following problems. That is to say, in the scanning method that requires changing an irradiation position, energy, and other irradiation parameters in order while changing apparatus component data settings according to the particular dose distribution, if the beam intensity of the beam transported to an irradiation device is too great, this could deteriorate irradiation accuracy since it may become impossible to follow up changed apparatus component data settings. Also, since narrow beams are used, instantaneous peak dose rates tend to increase, so it is desirable that partly in terms of safety during medical treatment irradiation, the beam intensity be moderately lowered. In addition, since the scanning method uses narrow beams, there is a need to suppress the beam size of the beams transported.

In the passive scattering method, however, since beams are spread by scattering devices and then directed to a target object, there are little problems with the irradiation accuracy and safety discussed above. To shorten the treatment time required, it is desirable that the beam intensity be moderately increased for higher dose rates. Therefore, beams whose irradiation parameters differ according to irradiation device should be transported to implement the medical treatment irradiation that is highly efficient and satisfies the irradiation accuracy and safety required of, for example, the above-mentioned charged particle beam irradiation apparatus having irradiation devices based on both scanning and passive scattering. In other words, data settings on the charged particle beam generator that generates charged particle beams are desirably modified according to the kind of irradiation device (i.e., the irradiation method) used for the treatment irradiation.

For the conventional charged particle beam irradiation apparatus having a plurality of irradiation devices, however, equivalent parameters such as beam intensity and beam size have always been used for the charged particle beam generator to emit beams to whichever irradiation device. For this reason, even when the conventional charged particle beam irradiation apparatus was provided with irradiation devices of different irradiation schemes such as scanning and passive scattering, it has been impossible to supply to the selected irradiation device the beams matching its irradiation scheme. Therefore, there has been room for improvement in terms of irradiation accuracy and safety.

The present invention was made in view of the above problems associated with the conventional technology, and an object of the invention is to provide: a charged particle beam irradiation apparatus capable of ensuring irradiation accuracy and safety, even if provided with the irradiation devices that use different irradiation methods; and a particle beam irradiation method used for the apparatus.

In order to achieve the above object, a charged particle beam irradiation apparatus of the present invention, designed to extract charged particle beams and emit the beams to an irradiation target, includes: a charged particle beam generator for generating the charged particle beams; a plurality of irradiation devices each for irradiating the irradiation target with the charged particle beams, wherein at least a part of the irradiation device group applies a different irradiation method; a beam transport system for transporting the charged particle beams extracted from the charged particle beam generator, to selected one of the irradiation devices; and a controller that modifies operating parameters of the charged particle beam generator according to the irradiation method adopted for the selected irradiation device.

In the present invention, charged particle beams suitable for the irradiation method adopted for the selected irradiation device can be transported thereto in order to modify operating parameters of the charged particle beam generator according to the above irradiation method. Irradiation accuracy and safety can thus be ensured.

Preferably, the irradiation apparatus further has a detector for detecting a beam state of the charged particle beams extracted from the charged particle beam generator, and a judging device for judging whether the beam state that has been detected is normal, and modifies judgment parameters of the judging device according to the irradiation method adopted for the selected irradiation device. This makes it possible to accurately judge whether the charged particle beams transported to the selected irradiation device are suitable for the irradiation method adopted therefor.

According to the present invention, irradiation accuracy and safety can thus be ensured, even if the irradiation apparatus has the irradiation devices that use different irradiation methods.

BRIEF DESCRIPTION OF THE DRAWINGS

Other objects and advantages of the invention will become apparent from the following description of embodiments with reference to the accompanying drawings in which:

FIG. 2 is a flowchart that shows process steps up to medical treatment irradiation;

FIG. 3 is a diagram that shows examples of the operating parameter data lists selected by a central controller and transmitted therefrom to an accelerator controller in process step 38 or 40 of FIG. 2;

DETAILED DESCRIPTION OF THE PREFERRED EMBODIMENTS

Embodiments of the present invention will be described in detail hereunder using the accompanying drawings.

First Embodiment

Figure 1:
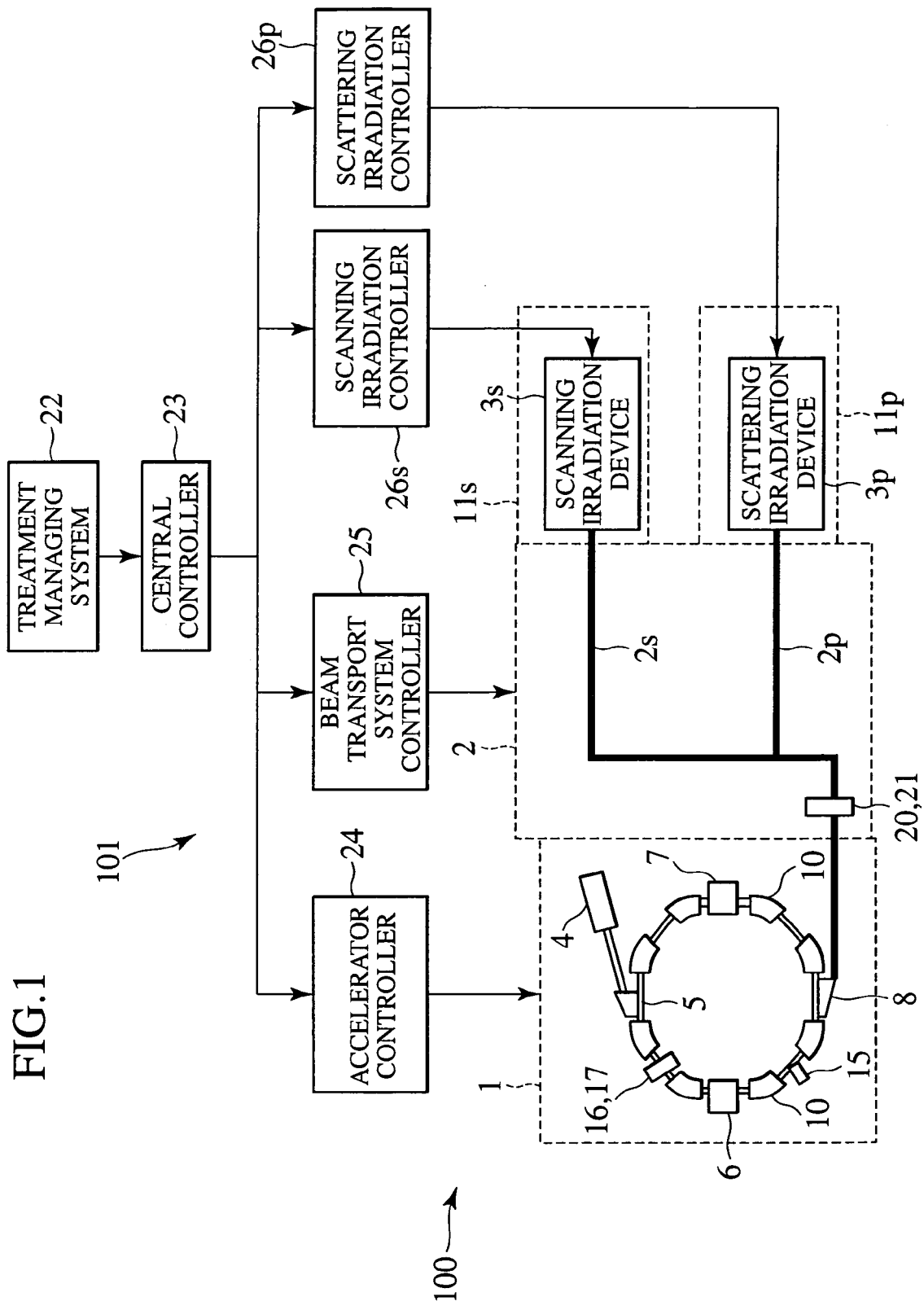
FIG. 1 is a total configuration diagram of a charged particle beam irradiation apparatus which is a preferred embodiment of the present invention.

First, a charged particle beam irradiation apparatus that is a preferred embodiment of the present invention is described below using FIG. 1.

A charged particle beam irradiation apparatus 100 of the present embodiment has a charged particle beam generator 1, a beam transport system 2 connected to an output end of the charged particle beam generator 1, and two irradiation devices, 3s and 3p, that operate as irradiation field forming devices. More specifically, the charged particle beam irradiation apparatus 100 of the present embodiment is a proton beam irradiation apparatus.

The charged particle beam generator 1 has an ion source (not shown), a pre-accelerator (e.g., a linear accelerator) 4, and a synchrotron 5 that is a main accelerator. In the synchrotron 5, a high-frequency beam extraction device 6 formed with one pair of electrodes, and a high-frequency beam accelerating cavity 7 are installed on a circular revolution orbit of ion beams. A first high-frequency power supply (not shown) is connected between the electrodes of the high-frequency beam extraction device 6, and an independent second high-frequency power supply (not shown) is provided for the high-frequency beam accelerating cavity 7. An ion beam, e.g., proton (or carbon ion) beam that has been generated by the ion source is accelerated by the pre-accelerator 4. After being extracted from the pre-accelerator 4, the ion beam (charged particle beam) enters the synchrotron 5. The ion beam, a charged particle beam, is accelerated by the energy applied according to particular strength of the electromagnetic field generated in the high-frequency beam accelerating cavity 7 by application of high-frequency electric power from the second high-frequency power supply. The ion beam that revolves inside the synchrotron 5 is accelerated to previously set energy (e.g., 100 to 200 MeV) and then extracted from the synchrotron 5. That is to say, high-frequency electric power from the first high-frequency power supply is applied to the revolving ion beam via the high-frequency beam extraction device 6. Accordingly, the ion beam revolving within safety limits moves out therefrom and is extracted through an extraction deflector 8. When the ion beam is extracted, an electric current conducted into quadrupole electromagnets (not shown) of the synchrotron 5 and into bending magnets 10 is maintained at an electric current data setting and the safety limits are also kept almost constant. The extraction of the ion beam from the synchrotron 5 is stopped by a stop of high-frequency electric power application to the high-frequency beam extraction device 6. Also, the first high-frequency power supply connected to the high-frequency beam extraction device 6 is controlled in accordance with the data settings prestored in association with the beam energy and beam intensity, and thus a beam of desired beam intensity is extracted from the synchrotron 5.

The two irradiation devices, 3s and 3p, are arranged in independent treatment rooms, and the ion beam from the charged particle beam generator 1 is transported to a selected treatment room by the beam transport system 2. The irradiation device 3p, one of the two irradiation devices, is a passive scattering irradiation device, and the irradiation device 3s that is the other of the two irradiation devices is a scanning irradiation device. Hereinafter, the treatment rooms where the irradiation devices 3p, 3s are arranged are called "scattering treatment room 11p" and "scanning treatment room 11s", respectively. Although not shown, a treatment bed for immobilizing a patient at an appropriate position, an X-ray fluoroscopic apparatus for obtaining fluoroscopic images of the patient, and other equipment are arranged in the treatment rooms 11p, 11s.

The synchrotron 5 also has a beam scraping device 15 on the orbit of the ion beam revolving in the synchrotron. The beam scraping device 15 has a scraper (not shown) that is a metallic block whose distance from the circular revolution orbit of the beam can be adjusted. Moving the scraper closer to the circular revolution orbit of the beam chips off a part of the beam for a reduced beam size. The synchrotron 5 further has a frequency monitor (detector) 16 for measuring a circular revolution frequency of the beam, a circular revolution orbit position monitor (detector) 17 for measuring a circular revolution orbit position, and a magnetic field monitor (not shown) for measuring magnetic field strength of the bending magnets of the synchrotron. The measurement results obtained from the monitors 16 and 17 after the ion beam has been accelerated are output to an accelerator controller 24 described later herein, and it is judged whether deviations between output measurement results and the prestored data settings mentioned above stay within an allowable range. In this way, the accelerator controller 24 judges whether the ion beam revolving in the synchrotron 5 has a desired beam energy level. If the output measurement results contain ones overstepping the allowable range, the accelerator controller 24 outputs an error signal to a central controller 23 described later herein. Thus, the central controller 23 controls the charged particle beam generator 1 via the accelerator controller 24 and directly decelerates the beam without extracting the beam. If all output measurement results are judged to stay within the allowable range, high-frequency electric power is applied to the high-frequency beam extraction device 6, whereby the extraction of the ion beam from the synchrotron 5 is started.

The ion beam that has been extracted from the synchrotron 5 is transported to the output end thereof by the beam transport system 2. The beam transport system 2 has a plurality of bending magnets (not shown) and quadrupole magnets (not shown), and beam paths 2p and 2s communicated with the passive scattering irradiation device 3p and scanning irradiation device 3s arranged in the two treatment rooms 11p and 11s, respectively. The quadrupole magnets and bending magnets constituting the beam transport system 2 are set so that in accordance with a command from a transport system controller 25 described later herein, the ion beam that has been extracted from the synchrotron 5 is transported to either the passive scattering irradiation device 3p or the scanning irradiation device 3s, whichever is selected. The ion beam, after being introduced into the beam transport system 2, is transported to the passive scattering irradiation device 3p through the beam path 2p or to the scanning irradiation device 3s through the beam path 2s.

The beam transport system 2 also includes a beam profile monitor (detector) 20 for measuring a position and width of the ion beam to be transported, and a beam intensity monitor (detector) 21 that measures intensity of an electric current of the beam to be transported. The transport system controller 25 acquires an output from the profile monitor 20 and an output from the beam intensity monitor 21, at fixed sampling time intervals. Next, the transport system controller 25 judges, by checking against the prestored data settings, whether the gravitational position and beam size of the beam, calculated from the output of the profile monitor 20, and the output of the beam intensity monitor 21 depart from the allowable range. If either of the outputs is judged to be outside the allowable range, an error signal is output to the central controller 23. Beam extraction is thus stopped.

Although this is not shown in the figure, the passive scattering irradiation device 3p provided in passive scattering treatment room 11p includes various constituent elements. Examples include: a scattering device for scattering a beam, a flatness monitor for measuring an as-scattered distribution of the beam, a dose monitor for measuring a beam energy dose, an energy modulation device for adjusting a depth-direction dose distribution, and a collimator for forming the beam into a necessary shape.

The ion beam that has been supplied via beam transport system 2p is spread in a direction vertical to a traveling direction of the beam, by the scattering device, and then adjusted to an appropriate energy distribution by the energy modulation device. Next, this beam is shaped by the collimator to fit to the shape of an affected region to be irradiated with the beam, and the patient who is the irradiation target is irradiated. When an integrated beam dose reaches a previously planned and set value, an ending signal of the irradiation is transmitted to the central controller 23. This completes the irradiation.

Although this is not shown in the figure, the scanning irradiation device 3s has scanning magnets for scanning a beam, a beam position monitor for measuring a position of the scanning beam, a dose monitor for estimating the irradiation dose, and other elements. An irradiation position of the ion beam that has been supplied via beam transport system 2s is adjusted by the scanning magnets, and then the patient who is the irradiation target is irradiated with the beam. The irradiation position and energy of the ion beam are previously planned and set as a parameter list associated with the integrated beam dose. As the integrated beam dose increases, the irradiation position and the energy are changed, and when the integrated beam dose reaches the previously planned and set value, an ending signal of the irradiation is transmitted to the central controller 23. This completes the irradiation.

The charged particle beam irradiation apparatus 100 of the present embodiment further has a control system 101. The control system 101 includes: a treatment managing system 22; a central controller (second controller) 23; an accelerator controller (judging device) 24 for controlling the charged particle beam generator 1; a transport system controller (judging device) 25 for controlling the beam transport system 2; a passive scattering irradiation controller 26p for controlling the passive scattering irradiation device 3p; and a scanning irradiation controller 26s for controlling the scanning irradiation device 3s.

The treatment managing system 22 has a database function to manage irradiation parameter data and irradiation schedules. Stored irradiation parameter data within the treatment managing system 22 differs according to the particular irradiation method. For the passive scattering method, the data consists of, for example, the energy, irradiation direction, irradiation range, irradiation dose, and other factors of the beam. For the scanning method, the energy, beam size, irradiation position, and other factors of the beam constitute list data associated with the integrated dose. The treatment managing system 22 is connected to an image acquisition system (not shown) that acquires the images used for CT and other diagnostic purposes, and to a patient information management database (not shown) that manages data on patients.

Process steps for medical treatment irradiation with the thus configured charged particle beam irradiation apparatus 100 of the present embodiment are described below using FIG. 2. FIG. 2 is a flowchart that represents process steps up to medical treatment irradiation.

Under user operations from the treatment room (step 31), the central controller 23 first reads in the irradiation parameter data required for next irradiation, from the treatment managing system 22 (step 32). The irradiation parameter data has been previously created by a treatment planning system (not shown) and registered in the treatment managing system 22. In step 32, the central controller 23 reads in irradiation parameter data for 3p if the user operations in step 31 are performed from passive scattering treatment room 11p, or reads in irradiation parameter data for 3s if the user operations are performed from scanning treatment room 11s. In this manner, it is discriminated whether the irradiation parameter data is for the passive scattering irradiation device 3p or for the scanning irradiation device 3s. Instead of this method, the irradiation parameter data itself may be endowed with information concerning the irradiation device (or the irradiation method), and the central controller 23 may be caused to conduct a discrimination based on the information.

In step 33, 34, or 35, it is judged whether discrepancies exist between the irradiation device information contained in the irradiation parameter data, and an operating location of the user. Processing is terminated in step 36 if discrepancies exist (e.g., if the irradiation parameter data for the scanning irradiation device 3s is called up from the passive scattering treatment room 11p, or vice verse).

Next, on the basis of the irradiation parameter data that it has read in, the central controller 23 selects operating parameter data on the charged particle beam generator 1 (synchrotron 5) and other constituent devices, from a pre-registered data list. Data that has thus been selected is transmitted to each controller (accelerator controller 24, transport system controller 25, and irradiation controller 26s, 26p) in step 37, 38, 39, or 40. For example, if attention is focused on the accelerator controller 24, the data list transmitted in the present embodiment is for scanning use or for passive scattering use. This data list includes the operation pattern data (magnet pattern IDs and others) of the synchrotron 5 that is associated with various energy levels, and information such as a high-frequency electric power output to be applied to the high-frequency beam extraction device 6 (see the description of FIG. 3, given later herein). The central controller 23 uses either the passive scattering data list if the irradiation parameter data is for passive scattering use, or the scanning data list if the irradiation parameter data is for scanning use, and acquires magnet pattern IDs and other operating parameter data from the beam energy data specified in the irradiation parameter data. Acquired operating parameter data is transmitted to the accelerator controller 24.

Each controller sets up each device on the basis of the operating parameter data transmitted from the central controller 23. After confirming completion of the setup, each controller transmits an irradiation ready signal to the central controller 23 (steps 41, 42). Thus, the central controller 23 makes irradiation startup operations valid and outputs a ready signal to computer terminals in each treatment room 11s, 11p. Subsequently, when an irradiation startup signal is output by user operations, operation of the synchrotron 5 is started and treatment irradiation based on data settings is initiated. If the setup of each device by each controller has not come to a normal end, an irradiation operational setup error occurs and processing is terminated (step 43).

The accelerator controller 24 controls the first highfrequency power supply on the basis of the data of highfrequency electric power (one of the operating parameter data) transmitted from the central controller 23. Thus the first high-frequency power supply outputs less electric power for irradiation by the scanning irradiation device 3s than for irradiation by the passive scattering irradiation device 3p. Because the less electric power is applied into the high-frequency beam extraction electric device 6, the smaller intensity ion beam extracted from the synchrotron 5 is supplied to the scanning irradiation device 3s. In addition, in the case that the scanning irradiation device 3s is selected, the accelerator controller 24 controls the position of the scraper 15 based on the data transmitted from the central controller 23 so as to reduce the beam size.

Examples of the operating parameter data lists selected by the central controller 23 and transmitted therefrom to the accelerator controller 24 in process step 38 or 40 of FIG. 2 are shown in FIG. 3. In the synchrotron 5 of the present embodiment, a spread of the ion beam revolving as mentioned above is increased by the application of high-frequency electric power to the high-frequency beam extraction device 6 and then extracted from the extraction deflector 8. It is possible, by adopting an extraction method that uses a high-frequency electric field in this way, to extract beams of a stable size and position, and to easily adjust beam intensity. As the high-frequency electric power increases, the ion beam spreads more rapidly and a rate of its injection into the beam deflector 8 also increases. This, in turn, increases the beam intensity of the ion beam extracted. In addition, since an ion beam of the lower beam energy spreads by the high-frequency electric field more rapidly, the beam intensity of the ion beam extracted by the same high-frequency electric power increases with a decrease in beam energy. As shown in FIG. 3, in the data list for passive scattering, data is set so that the high-frequency electric power decreases with a decrease in beam energy and so that almost constant beam intensity is extracted, regardless of the energy. In association with this, an upper limit of the beam intensity is also fixed at a constant value. In the data list for scanning, data is set so that the high-frequency electric power decreases below of passive scattering and so that the beam intensity of the ion beam extracted is diminished with decreases in beam energy. In association with this, the beam intensity upper limit is set to totally decrease in comparison with that of passive scattering and to be lowered with decreases in beam energy.

Also, the scraper position shown in FIG. 3 is distanced from the circular revolution orbit of the beam on the scraper, as mentioned earlier. Longer distance from the orbit means that the amount of beam chipped is smaller. In the present embodiment, the above distance for passive scattering is set to such a value that does not limit the beam size, and the above distance for scanning is set to such a value that reduces the beam size by chipping the beam. In this way, little beams are chipped for the passive scattering irradiation method that requires a large number of beams, and the beam size is reduced for the scanning irradiation method that requires narrow beams.

In addition, a circular revolution frequency range of the ion beam is set to a large value for passive scattering, and a small value for scanning. In this way, a wide allowable energy range is employed for the passive scattering method that does not deteriorate irradiation accuracy too significantly with respect to a change in beam energy, and a narrow allowable energy range is employed for the scanning method.

Although this is not shown in FIG. 3, in the operating parameter data list transmitted from the central controller 23 to the transport system controller 25, an allowable beam position setting range for irradiation in the passive scattering treatment room 11p is wider than for irradiation in the scanning treatment room 11s.

Figures 4, 5:
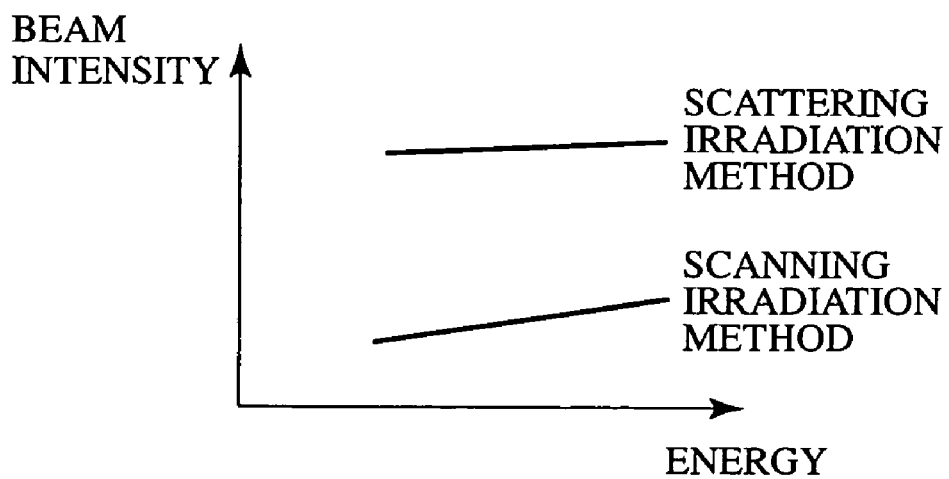
FIG. 4 is a diagram in which, in the charged particle beam irradiation apparatus of the present embodiment, features of the operating parameter data list transmitted from the central controller to the accelerator controller are represented so that differences between a passive scattering irradiation method and a scanning irradiation method can better be understood.
FIG. 5 is a diagram showing the relationship between the beam energy data and to-be-extracted beam intensity data specified in an operating parameter data list for passive scattering and in an operating parameter data list for scanning.

FIG. 4 is a diagram in which features of the operating parameter data list transmitted to the central controller 24 and accelerator controller 25 in the present embodiment described above are represented so that differences between the passive scattering irradiation method and the scanning irradiation method can better be understood. As shown in FIG. 4, the set beam intensity value and set beam size value transmitted to the accelerator controller 24 and used for irradiation in the passive scattering treatment room 11p are greater than for irradiation in the scanning treatment room 11s. The allowable energy range data and allowable beam position range data transmitted to the accelerator controller 24 and the transport system controller 25, respectively, for irradiation in the passive scattering treatment room 11p are also greater than for irradiation in the scanning treatment room 11s.

The charged particle beam irradiation apparatus 100 of the present embodiment offers the following advantageous effects. That is, in the passive scattering irradiation method, irradiation accuracy does not greatly depend on the intensity of the beam current from the charged particle beam generator 1. This is because states of the beams for the irradiation of the patient (i.e., the spread and energy distribution of the beams) are typically determined by specifications of the scattering device, energy modulation device, collimator, and other devices arranged for the irradiation apparatus. In addition, changes in dose distribution are small with respect to changes in beam energy. For these reasons, increases in the beam intensity or slight variations in beam energy do not deteriorate irradiation accuracy very much.

In the scanning irradiation method, however, irradiation positions, energy, and other irradiation parameters are sequentially changed according to the integrated dose, so if the beam intensity of the beam transported to the irradiation device is too great, devices become unable to follow up too quick parameter change and irradiation accuracy would be deteriorated. Also, since narrow beams are used, instantaneous peak dose rates tend to increase, so it is desirable that partly in terms of safety during medical treatment irradiation, the beam intensity be moderately lowered. In addition, since the scanning method uses narrow beams, there is a need to suppress the beam size of the beams transported.

For these reasons, in the charged particle beam irradiation apparatus 100 having both passive scattering and scanning types of irradiation devices 3s and 3p as in the present embodiment, beams whose irradiation parameters differ according to a particular irradiation method need to be supplied to associated irradiation device 3s or 3p to conduct the treatment irradiation that satisfies the irradiation accuracy and safety required.

In the charged particle beam irradiation apparatus 100 of the present embodiment, therefore, as described above, charged particle beams suitable for the irradiation method adopted for a selected irradiation device can be supplied to the irradiation device 3s or 3p in order to modify the operating parameters of the charged particle beam generator 1. It is thus possible to ensure irradiation accuracy and safety. Since the circular revolution frequency range of the ion beam is set to a large value for passive scattering, and a small value for scanning, it is also possible to enhance irradiation efficiency by employing a wide allowable energy range for the passive scattering method that does not deteriorate irradiation accuracy too significantly with respect to a change in beam energy. In addition, it is possible to monitor for necessary irradiation accuracy by employing a narrow allowable energy range for the scanning method. For these reasons, irradiation accuracy and safety can be reliably secured.

Furthermore, in the present embodiment, the data list for scanning is set so that as described above, beam intensity is lowered with decreases in beam energy. The relationship between the beam energy data and to-be-extracted beam intensity data specified in the operating parameter data list for passive scattering and in the operating parameter data list for scanning is shown in FIG. 5. Since, as can be seen from this figure, the data list for scanning is set so that beam intensity is lowered with decreases in beam energy, beam intensity can be appropriately set for and monitored during the scanning irradiation that requires controlling the beam intensity to a small value for using narrow beams. This allows irradiation accuracy and safety to be secured more reliably.

While it has been described heretofore that an upper-limit value is not provided for the high-frequency beam extraction electric power applied by the high-frequency beam extraction device 6, an upper limit of high-frequency beam extraction electric power for irradiation by the scanning irradiation device 3s may be set to a value smaller than an upper limit of high-frequency beam extraction electric power for irradiation by the passive scattering irradiation device 3p. This allows reliable limitation of the extraction current supplied in the scanning method, and hence, further improvement of safety.

It has also been described heretofore that beam intensity is adjusted according to a particular high-frequency beam extraction electric power level and that the beam size is adjusted by the beam scraping device 15. When the beam is chipped by inserting a scraper, the beam is narrowed down and at the same time, the beam current inside the synchrotron 5 decreases to diminish the beam intensity of the beam extracted. This property may be utilized to adjust the beam intensity and the beam size at the same time according to the amount of scraper insertion by the beam scraping device 15.

In addition, although only setup parameters equivalent to one kind of beam intensity for each beam energy level are shown in FIG. 3, specification of irradiation parameter data or selection of beam intensity by an operator may be conducted after a plurality of beam intensity values have been provided. In that case, the high-frequency beam extraction electric power level may be changed according to the beam intensity selected, and at the same time, changes may also be made to an upper-limit value of the beam intensity, a position of the scraper, and other parameters. Thus, greater flexibility in response to a request for more advanced treatment irradiation can be obtained and at the same time, irradiation accuracy and safety can be improved.

Furthermore, while an example of providing two kinds of data lists, one for scanning irradiation and one for passive scattering irradiation, is shown in the present embodiment, it may also be possible to provide a larger number of kinds of data lists, including those intended for irradiation devices of different irradiation field sizes, or to provide independent data lists for each treatment room. Thus, even in a system that requires beams whose irradiation parameters differ, it is possible to realize each of the parameters automatically and appropriately and to improve accuracy and safety.

In the case that the size of the ion beam extracted from the synchrotron 5 is adequately narrow for the scanning irradiation, it may also be possible to apply the same setting of the beam size for both scanning irradiation and passive scattering irradiation. In this case, it is also possible to control the beam intensity in accordance with the selected irradiation device. Specifically for present embodiment, as described above, it can be realized by setting the first highfrequency power supply so that it output less electric power for irradiation by the scanning irradiation device 3s than for irradiation by the passive scattering irradiation device 3p.

Second Embodiment

A charged particle beam irradiation apparatus that is another embodiment of the present invention is described below using FIG. 6. Charged particle beam irradiation apparatus 100A of the present embodiment is adapted to include: a charged particle beam generator 1A with a cyclotron 5A, instead of the charged particle beam generator 1 with a synchrotron 5 in the charged particle beam irradiation apparatus 100; and a control system 101A with an added second passive scattering treatment room, an operational state monitoring device (judging device) 45, and an added second passive scattering irradiation controller for the added treatment room, instead of the control system 101 in the irradiation apparatus 100.

The charged particle beam irradiation apparatus 100A has the charged particle beam generator 1A equipped with the cyclotron 5A by which incident beams from an ion source (not shown) are accelerated to desired energy, a beam transport system 2A connected to an output end of the charged particle beam generator 1A, and three irradiation treatment rooms. The three irradiation treatment rooms are a scanning treatment room 11s with an installed scanning irradiation device 3s, and passive scattering treatment rooms 11p1 and 11p1 with installed passive scattering irradiation devices 3p1 and 3p2, respectively. The cyclotron 5A that generates beams of fixed energy as charged particle beams essentially of a continuous current, has an energy adjusting system (energy selection system) 46 for degrading and selecting the beams.

The energy adjusting system 46, although described hereinafter as being included in the charged particle beam generator 1A, may be included in a beam transport system 2.

The beams of fixed energy that have been extracted from the cyclotron 5A through a beam deflector 47 have the energy absorbed by a degrader 48, thus providing desired energy necessary for irradiation. The beams that have been significantly scattered by the degrader 48 are cut by an emittance aperture 49, then bent by an energy analyzing magnet 50, and beams whose energy has deviated from the desired energy are cut by an energy aperture device 51. The degrader 48, the emittance aperture 49, the energy analyzing magnet 50, and the energy aperture device 51 constitute the energy adjusting system 46 that selects beam energy and adjusts a beam size. In the energy aperture device 51, plural kinds of apertures with different aperture sizes are selectively provided and these apertures are each selected by an accelerator controller 24, whereby the beam size is controlled. The energy analyzing magnet 50 has an energy-analyzing magnetic field monitor (not shown), by which the energy of the beams is monitored.

Beam transport system 2A has beam paths 2p1, 2p2, and 2s, which are communicated with the passive scattering irradiation devices 3p1, 3p2 and scanning irradiation device 3s arranged in the three treatment rooms, 11p1, 11p2, and 11s, respectively. In the beam transport system 2A, similarly to the first embodiment, a beam profile monitor 20 and a beam intensity monitor 21 are arranged to monitor a state of the beam.

In addition to the control system components in the first embodiment, the control system 101A has an operational state monitoring device 45. The operational state monitoring device 45 reads an output of an energy-analyzing magnetic field monitor (not shown) provided at the energy analyzing magnet 50, an output of the profile monitor 20 in the beam transport system 2A, and an output of the beam intensity monitor 21, at fixed sampling time intervals. Next, the operational state monitoring device 45 judges, by checking against prestored data settings, whether the gravitational position and beam size of the beam, calculated from the magnetic field monitor output and the output of the profile monitor 20, deviate from an allowable range. If either of the outputs is judged to be outside the allowable range, an error signal is output to a central controller 23, thus causing the synchrotron 5A to stop supplying beams.

Apparatus components other than those described above, and irradiation process steps are basically the same as in the first embodiment. In the present second embodiment, however, the charged particle beam generator 1A includes the synchrotron 5A and the energy adjusting system 46, so the kinds of operating parameter data items transmitted from the central controller 23 to the accelerator controller 24 differ as described below.

On the basis of the irradiation parameter data that it has read in, the central controller 23, as with that of the first embodiment, selects operating parameter data on the charged particle beam generator 1A (cyclotron 5A) and other constituent devices, from a pre-registered data list. Data that has thus been selected is transmitted to each controller, that is, an accelerator controller 24, transport system controller 25, and irradiation controller 26s, 26p1, 26p2. Either a data list for scanning, or a data list for passive scattering is transmitted to the accelerator controller 24. Each such data list includes information such as: ion source electric-current data settings associated with various energy levels, operational data on the energy analyzing magnet 50, and the kinds of apertures in the energy aperture device 51.

Figure 6:
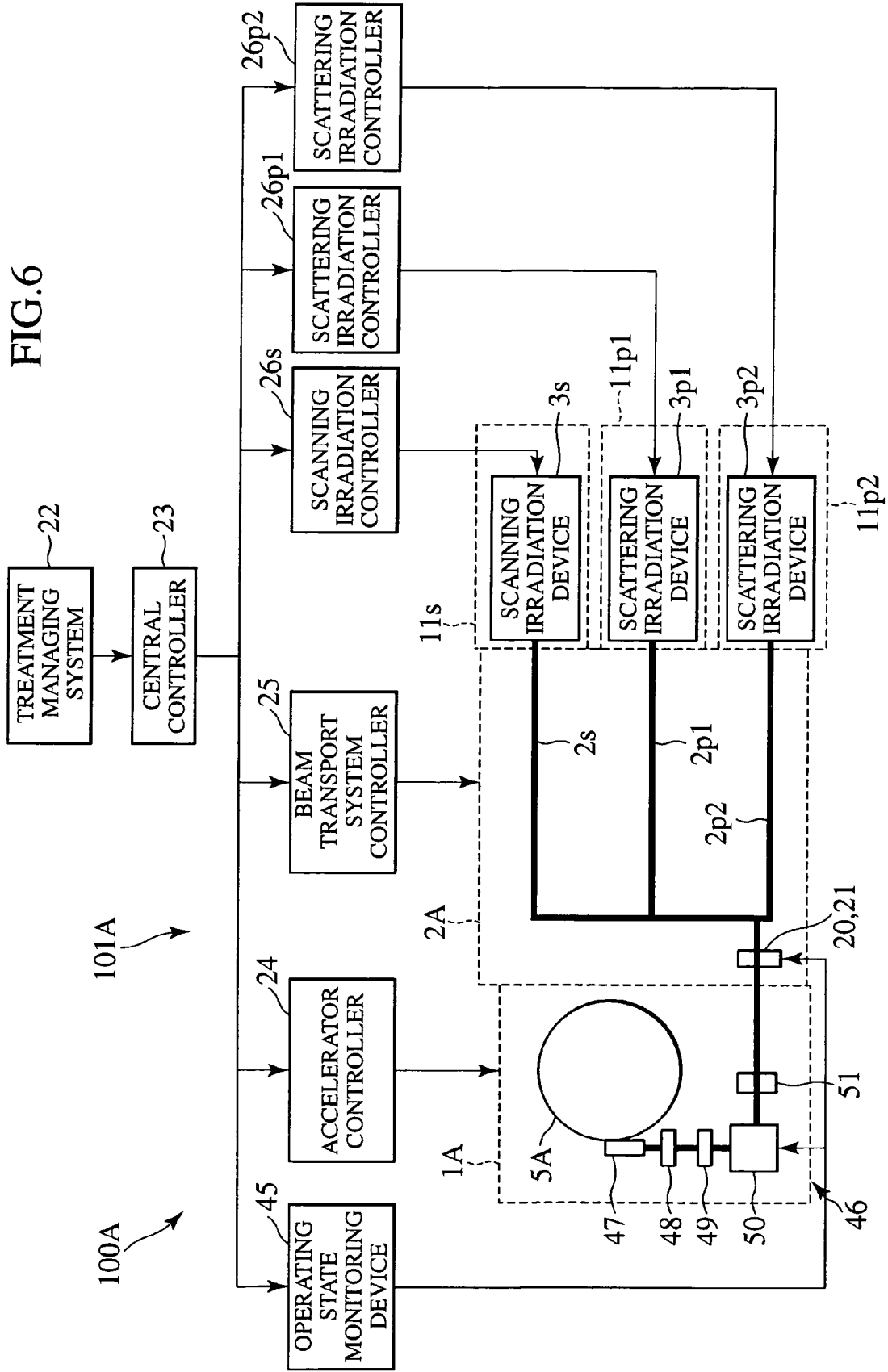
FIG. 6 is a total configuration diagram of a charged particle beam irradiation apparatus which is another embodiment of the present invention.

Although this is not shown in FIG. 6, in the present embodiment, electric-current data settings for the ion source are relatively high for passive scattering, and relatively small for scanning. Also, the kinds of apertures in the energy aperture device 51 are set so that for passive scattering, each aperture takes a large aperture size, and so that for scanning, beams are chipped and dimensionally narrowed down for each aperture.

Thus, an allowable energy range for passive scattering is spread and that of scanning is narrowed. Also, in the operating parameter data list transmitted from the central controller 23 to the transport system controller 25, an allowable beam position setting range for passive scattering is wider than that of scanning.

As can be seen from the above, similarly to the first embodiment, as shown in FIG. 4, the set beam intensity value and set beam size value transmitted to the accelerator controller 24 and used for irradiation in the passive scattering treatment room 11p1, 11p2, are greater than for irradiation in the scanning treatment room 11s. The allowable energy range data and allowable beam position range data transmitted to the accelerator controller 24 and the transport system controller 25, respectively, for irradiation in the passive scattering treatment room 11p1, 11p2, are also greater than for irradiation in the scanning treatment room 11s.

Irradiation accuracy and safety, therefore, can also be ensured in the present embodiment. Additionally, according to the present embodiment, energy, beam intensity, beam positions, width, and other parameters representing an operational state are monitored by the operational state monitoring device 45 provided independently of the accelerator controller 24 and the transport system controller 25. This allows a desired operational state to be monitored for, even in case of a single failure such as a malfunction in the accelerator controller 24, and thus, safety to be improved further.

It has also been described heretofore that beam intensity is adjusted by setting the ion source electric-current and that the beam size is adjusted by selecting an aperture device 51. When beam size is adjusted by the aperture device 51, the beam is narrowed down and at the same time, the beam intensity pass through the aperture device 51 is decreased. This property may be utilized to adjust the beam intensity and the beam size at the same time according to the selecting an aperture device 51. In the case that the size of the ion beam extracted from the cyclotron 5A is adequately narrow for the scanning irradiation, it may also be possible to apply the same setting of the beam size for both scanning irradiation and passive scattering irradiation. In this case, it is also possible to control the beam intensity in accordance with the selected irradiation device. Specifically for present embodiment, it can be realized by setting the ion source electric-current data so that it output less ion beam for irradiation by the scanning irradiation device 11s than for irradiation by the passive scattering irradiation device 11p1 or 11p2.

While operating parameters on high-frequency beam extraction electric power, on a beam current upper limit, on a scraper position, on frequency ranges, on ion source electric-current data settings, and on the kinds of apertures, are designed so as to be modified in the two embodiments described above, the present invention is not limited to/by this modification form and other operating parameters may also be modified. Irradiation accuracy and safety can likewise be improved by assigning appropriate data to other parameters as well, irrespective of whether scanning or passive scattering is employed.

While the invention has been described in its preferred embodiments, it is to be understood that the words which have been used are words of description rather than limitation and that changes within the purview of the appended claims may be made without departing from the true scope and spirit of the invention in its broader aspects.

What is claimed is:

1. A charged particle beam irradiation apparatus that irradiates an irradiation target with a charged particle beam, said apparatus comprising:
   a charged particle beam generator for generating the charged particle beam according to operating parameters, the charged particle beam generator including a beam reducing device for reducing the beam size of the charged particle beam;
   a plurality of irradiation devices including an irradiation device that employs a scanning irradiation method and an irradiation device that employs a passive scattering irradiation method, each irradiation device for irradiating the irradiation target with the charged particle beam;
   a beam transport system for transporting the charged particle beam extracted from said charged particle beam generator, to a selected one of said irradiation devices; and
   a controller for determining the operating parameters of said charged particle beam generator according to the irradiation method of the selected irradiation device and irradiation parameters for the selected irradiation device,
   said controller comprises a computer readable medium containing instructions that, when executed, cause the controller to determine operating parameters for controlling the beam reducing device based on the irradiation method of the selected irradiation device, wherein the beam reducing device reduces the beam size said charged particle beam when said selected irradiation device employs the scanning irradiation method so that the beam intensity and beam size of the charged particle bean that exist when an irradiation device employing the scanning irradiation method is selected will be smaller than the beam intensity and beam size existing when an irradiation device employing the passive scattering irradiation method is selected.

2. The charged particle beam irradiation apparatus according to claim 1, further including:
   a detector for detecting a beam state of the charged particle beam extracted from said charged particle beam generator; and
   a judging device for judging whether the beam state that has been detected is normal;
   wherein said controller modifies judgment parameters of said judging device according to the irradiation method adopted for said selected irradiation device.

3. The charged particle beam irradiation apparatus according to claim 2, wherein:
   said detector detects a beam energy level and beam position of the charged particle beam;
   said judging device judges whether detection results by said detector stay within allowable ranges; and
   said controller modifies the allowable ranges used as judgment criteria by said judging device, according to the irradiation method adopted for said selected irradiation device.

4. The charged particle beam irradiation apparatus according to claim 3, wherein said controller modifies judgment parameters of said judging device so that the allowable beam energy and beam position ranges used as judgment criteria by said judging device when an irradiation device employing the scanning irradiation method is selected will be narrower than the allowable ranges used as judgment criteria when an irradiation device employing the passive scattering irradiation method is selected.

5. The charged particle beam irradiation apparatus according to claim 4, wherein said charged particle beam generator includes a synchrotron.

6. The charged particle beam irradiation apparatus according to claim 5, wherein:
   said charged particle beam generator includes said synchrotron having a high-frequency beam extraction device for extracting the charged particle beam by applying high-frequency electric power to the beam; and
   said controller operates such that the voltage applied to said high-frequency beam extraction device when an irradiation device employing the scanning irradiation method is selected will be lower than the voltage applied when an irradiation device employing the passive scattering irradiation method is selected.

7. A charged particle beam irradiation apparatus that irradiates an irradiation target with a charged particle beam, said apparatus comprising:
   a charged particle beam generator for generating the charged particle beam;
   a plurality of irradiation devices each for irradiating the irradiation target with the charged particle beam;
   a beam transport system for transporting the charged particle beam extracted from said charged particle beam generator, to selected one of said irradiation devices;
   a controller that modifies operating parameters of said charged particle beam generator;
   a detector for detecting a beam state of the charged particle beam extracted from said charged particle beam generator; and
   a judging device for judging whether the beam state that has been detected is normal,
   wherein said plurality of irradiation devices include an irradiation device that employs a scanning irradiation method and an irradiation device that employs a passive scattering irradiation method,
   said controller is adapted to modify operating parameters of said charged particle beam generator according to said selected irradiation device that employs the scanning irradiation method or the passive scattering irradiation method,
   said controller modifies operating parameters of said charged particle beam generator so that the beam intensity and beam size of the charged particle beam that exist when an irradiation device employing the scanning irradiation method is selected will be smaller than the beam intensity and beam size existing when an irradiation device employing the passive scattering irradiation method is selected,
   said controller modifies judgment parameters of said judging device according to the irradiation method adopted for said selected irradiation device,
   said detector detects a beam energy level and beam position of the charged particle beam,
   said judging device judges whether detection results by said detector stay within allowable ranges,
   said controller modifies the allowable ranges used as judgment criteria by said judging device, according to the irradiation method adopted for said selected irradiation device,
   said controller modifies judgment parameters of said judging device so that the allowable beam energy and beam position ranges used judgment criteria by said judging device when an irradiation device employing the scanning irradiation method is selected will be narrower than the allowable ranges used as judgment criteria when an irradiation device employing the passive scattering irradiation method is selected, said charged particle beam generator includes a synchrotron, said charged particle beam generator includes said synchrotron having a beam scraping device which, by inserting a beam scraper, cuts a part of the charged particle beam while the beam is circularly revolving within said synchrotron, and said controller operates such that a stroke through which the beam scraper is inserted by said beam scraping device when an irradiation device employing the scanning irradiation method is selected will be greater than a stroke through which the beam scraper is inserted when an irradiation device employing the passive scattering irradiation method is selected.

8. The charged particle beam irradiation apparatus according to claim 2, further including a second controller which, if said judging device judged that the charged particle beam extracted from said charged particle beam generator is abnormal, stops further extraction of charged particle beams from said charged particle beam generator.

9. A charged particle beam irradiation apparatus that irradiates an irradiation target with a charged particle beam said apparatus comprising:

a charged particle beam generator including at cyclotron which accelerates the charged particle beam, said charged particle beam generator comprising an aperture device for cutting out a part of the charged particle beam;

a plurality of irradiation devices each for irradiating the irradiation target with the charged particle beam;

a beam transport system for transporting the charged particle beam extracted from said charged particle beam generator, to a selected one of said irradiation devices; and a controller comprising a computer readable medium containing instructions that, when executed, cause said controller to select data settings for operating parameters of said charged particle beam generator and aperture device from a predetermined data list based on the irradiation method of the selected irradiation device and stored irradiation parameters for the selected irradiation device, wherein said charged particle beam generator includes an ion source for emitting the charged particle beam to said cyclotron, said plurality of irradiation devices include an irradiation device that employs a scanning irradiation method and an irradiation device that employs a passive scattering irradiation method, and said data settings of said operating parameters result in the charged particle beam having a smaller beam intensity and beam size when the selected irradiation device employs a scanning irradiation method than when the selected irradiation device employs a passive scattering irradiation method.

10. The charged particle beam irradiation apparatus according to claim 9, further including:

an energy adjusting system that changes energy of the charged particle beam extracted from said cyclotron;

wherein said controller modifies operating parameters of said charged particle beam generator or of said energy adjusting system according to the irradiation method adopted for said selected irradiation device.

11. The charged particle beam irradiation apparatus according to claim 10, wherein;

said energy adjusting system includes said aperture device in which plural kinds of apertures each for cutting part of the charged particle beam extracted from said cyclotron are selectively equipped; and said controller selects each of the apertures such that the amount of beam cut when an irradiation device employing the scanning irradiation method is selected will be greater than the amount of beam cut when an irradiation device employing the passive scattering irradiation method is selected.

12. A method of charged particle beam irradiation in which the charged particle beam generated by a charged particle beam generator is emitted in transported form to selected one of plural irradiation devices whose irradiation methods include a different irradiation method, wherein operating parameters of the charged particle beam generator are selected from a predetermined data list according to the irradiation method adopted for the selected irradiation device and stored irradiation parameter data; and said operating parameters of the charged particle beam generator are selected so that the beam intensity and beam size of the charged particle beam that is transported to the selected irradiation device will be smaller when the selected irradiation device employs the scanning irradiation method than when the selected irradiation device employs the passive scattering irradiation method.

13. The charged particle beam irradiation method according to claim 12, wherein judgment parameters for judging whether a beam state of the charged particle beam extracted from the charged particle beam generator is normal are modified according to the irradiation method adopted for the selected irradiation device.

14. The charged particle beam irradiation method according to claim 13, wherein allowable ranges for judging whether a beam energy level and beam position of the charged particle beam are normal are modified according to the irradiation method adopted for the selected irradiation device.

15. A method of charged particle beam irradiation in which the charged particle beam generated by a charged particle beam generator which includes a cyclotron and an ion source for emitting the charged particle beam to said cyclotron is emitted in transported form to selected one of plural irradiation devices whose irradiation methods include the scanning irradiation method and the passive scattering irradiation method;

wherein data settings for operating parameters of the charged particle beam generator and of the beam transport are selected according to the irradiation method adopted for the selected irradiation device, and said selected data settings result in the charged particle beam that is emitted in transported form to the selected irradiation device to have a smaller beam intensity and beam size when the selected irradiation device employs a scanning irradiation method than when the selected irradiation device employs a passive scattering irradiation method.

* * * * *